US008676315B2

(12) United States Patent
Warner et al.

(10) Patent No.: US 8,676,315 B2
(45) Date of Patent: Mar. 18, 2014

(54) SYSTEM AND METHOD OF ELECTRICAL CURRENT DETECTION IN ELECTROPHYSIOLOGY STUDY

(75) Inventors: Adrian F. Warner, Wauwatosa, WI (US); Daniel R. Schneidewend, Wauwatosa, WI (US); Claudio P. Mejia, Wauwatosa, WI (US); Timothy P. Stiemke, Wauwatosa, WI (US); Rodger F. Schmit, Wauwatosa, WI (US); Aaron J. Hill, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 5 days.

(21) Appl. No.: 13/190,829

(22) Filed: Jul. 26, 2011

(65) Prior Publication Data

US 2013/0030482 A1 Jan. 31, 2013

(51) Int. Cl.
*A61N 1/08* (2006.01)

(52) U.S. Cl.
USPC .......... 607/17

(58) Field of Classification Search
USPC .......... 607/17
See application file for complete search history.

(56) References Cited

U.S. PATENT DOCUMENTS

| | | | | |
|---|---|---|---|---|
| 3,363,144 | A | 1/1968 | Carter et al. | |
| 4,807,639 | A | 2/1989 | Shimizu et al. | |
| 5,431,691 | A | 7/1995 | Snell et al. | |
| 6,917,832 | B2 | 7/2005 | Hutten | |
| 7,020,530 | B1 | 3/2006 | Ideker et al. | |
| 7,640,059 | B2 | 12/2009 | Forsberg et al. | |
| 2002/0116034 | A1 | 8/2002 | Miller et al. | |
| 2003/0078510 | A1 | 4/2003 | Olson et al. | |
| 2005/0131473 | A1 | 6/2005 | Gordon et al. | |
| 2006/0004424 | A1 | 1/2006 | Loeb et al. | |
| 2006/0247550 | A1 | 11/2006 | Thiagarajan et al. | |
| 2007/0073349 | A1 | 3/2007 | Conley et al. | |
| 2008/0058794 | A1 | 3/2008 | MacAdam et al. | |
| 2008/0281312 | A1* | 11/2008 | Werneth et al. | 606/33 |
| 2012/0109242 | A1* | 5/2012 | Levin et al. | 607/17 |

FOREIGN PATENT DOCUMENTS

| | | |
|---|---|---|
| EP | 1393773 A1 | 3/2004 |

OTHER PUBLICATIONS

Unofficial Translation of Search Report and Written Opinion from FR Application No. 1257237 dated Mar. 1, 2013.

* cited by examiner

*Primary Examiner* — Joseph Stoklosa
*Assistant Examiner* — Minh Duc Pham

(57) ABSTRACT

A system in combination with a stimulator system and an electrophysiology recorder system in delivering a stimulator signal to a subject's heart is provided. The electrophysiology recorder system can be generally operable to acquire an electrocardiogram from the subject's heart. The system can include an electrical couple in electrical connection between the simulator system and the electrophysiology recorder. The electrical couple can be configured to communicate the stimulator signal without loading an impedance of the electrophysiology recorder system on the stimulator system.

9 Claims, 3 Drawing Sheets

SYSTEM AND METHOD OF ELECTRICAL CURRENT DETECTION IN ELECTROPHYSIOLOGY STUDY

FIELD OF USE

The subject matter generally relates to a system and method of electrical current detection, and more particularly to a system and method of detecting electrical current detection in an electrophysiology study.

BACKGROUND

Referring to FIG. 1, complex arrhythmias, such as Atrial Fibrillation or Ventricular Tachycardia, may require concurrent use of a cardiac stimulator system 10 in combination with an electrophysiology (EP) recording system 15 and an electrical mapping system 20 in study of a subject's heart 25. The cardiac stimulator system 10 can be used to direct an application of a stimulator or pace signal 28 by the cardiac stimulator system 10 via catheters 30 and 32 at various anatomical features or locations of the heart 25. The electrical mapping system 20 can be used to record an electrical activation on either a pseudo-anatomical model of the heart 25, or on a previously acquired anatomical image of the heart 25 during the procedure to stimulate the heart 25. The EP recording system 15 can be used to record surface or intracardiac electrocardiogram signals and various other patient vital physiological data of the subject during the cardiac stimulation procedure. The output of the EP recording system 15 can be used to document the patient case, and may also be used by the physician to help determine the appropriate position/location of the catheters 30, 32 in application of the stimulation signal derived from the cardiac stimulator system 10 relative to various locations of the heart 25.

During the above-described procedure, several drawbacks can occur. One drawback can be an increased likelihood of conflict over routing of the stimulator signal 28 through the EP recorder and electrical mapping systems 15 and 20 to the heart 25. Another drawback can be increased electrical loading on the cardiac stimulator device 10 associated with the stimulator signal 28 routing through the EP recorder and electrical mapping systems 15 and 20, and their respective amplifiers. Other drawbacks includes an increased likelihood of noise associated with the wiring and a reduced common mode rejection of amplifiers with the coupling of the impedance from the EP recorder and electrical mapping systems 15 and 20 associated with the known technique to connect the EP recording electrical mapping systems 15 and 20 with the cardiac stimulator system 10. The above-described drawbacks can increase a likelihood of increased noise attenuation and degraded detection of the stimulator signal 28 in combination with recording the ECG (e.g., surface and/or intracardiac) signal during such a procedure.

BRIEF SUMMARY

There is a need or desire for a system to record an electrocardiogram (ECG) signal (e.g., surface and/or intracardiac) in combination with an electrical mapping system during application of an electrical stimulator signal via catheters to the heart having reduced electrical loading on the electrical stimulator system and that lowers the likelihood of noise attenuation and degradation of detection of the stimulator signal with recording of the ECG signal during such a procedure to electrically stimulate the heart of a subject. The above-mentioned drawbacks and needs are addressed by the embodiments described herein in the following description.

According to one embodiment of the subject matter described herein, a system in combination with a stimulator system and an electrophysiology recorder system in delivering a stimulator signal to a subject's heart is provided. The electrophysiology recorder system can be generally operable to acquire an electrocardiogram from the subject's heart. The system can include an electrical coupling in electrical connection between the simulator system and the electrophysiology recorder. The electrical couple can be configured to communicate the stimulator signal without loading an impedance of the electrophysiology recorder system on the stimulator system.

According to another embodiment of the subject matter described herein, a system to deliver a stimulator signal to a subject's heart is provided. The system can include an electrical stimulator system that generates the stimulator signal; an electrophysiology mapping system that communicates the stimulator signal to the subject's heart; an electrophysiology mapping system; and a system indirectly connecting the stimulator system and the electrophysiology mapping system to the electrophysiology recorder system such that the electrophysiology recorder system creates a display of detection of the stimulator signal in combination with an electrocardiogram of the subject's heart without the electrophysiology recorder system directly receiving the stimulator signal.

According to yet another embodiment of the subject matter described herein, a method of delivering a stimulator signal to subject's heart is provided. The method can include the steps of: communicating the stimulator signal through an electrophysiology mapping system for delivery by a catheter to the heart of a subject; creating an anatomical map of a location of delivery of the stimulator signal to the subject's heart; and creating a display at an electrophysiology recorder that includes an illustration of an occurrence of the delivery of the stimulator signal to the subject's heart in combination with an illustration of an electrocardiogram waveform acquired from the subject while delivering the stimulator signal, wherein the electrophysiology recorder is not in electrical connection to receive the stimulator signal.

According to yet another embodiment of the subject matter described herein, a system that detects an occurrence of a stimulator signal delivered by a stimulator system via an electrophysiology mapping system to a subject's heart for illustration on a display in real-time in combination with real-time acquisition of an electrocardiogram of the subject's heart by an electrophysiology recorder system for illustration on the display is provided. The system performs the above without loading an impedance of the electrophysiology recorder system on the delivery of the stimulator signal to the subject's heart.

Systems and methods of varying scope are described herein. In addition to the embodiments described in this summary, further embodiment may become apparent by reference to the drawings and with reference to the detailed description that follows.

DETAILED DESRIPTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
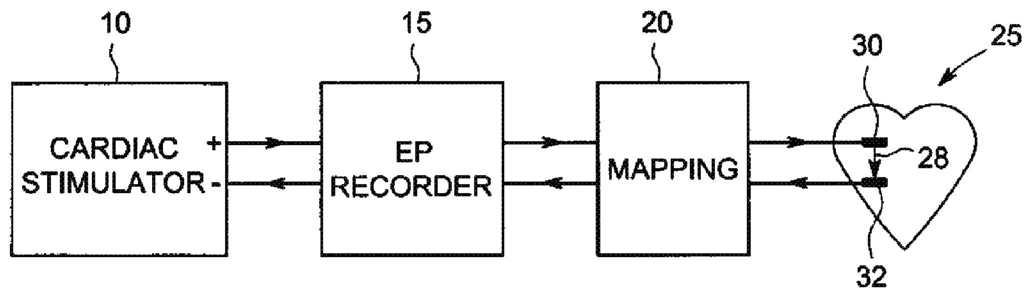
FIG. 1 shows a schematic diagram of a known system in the prior art that includes a cardiac stimulator system connected in combination with an EP mapping system and an EP recording system in a procedure to apply a stimulator signal via a catheter to various locations of a subject's heart.
Figure 2:
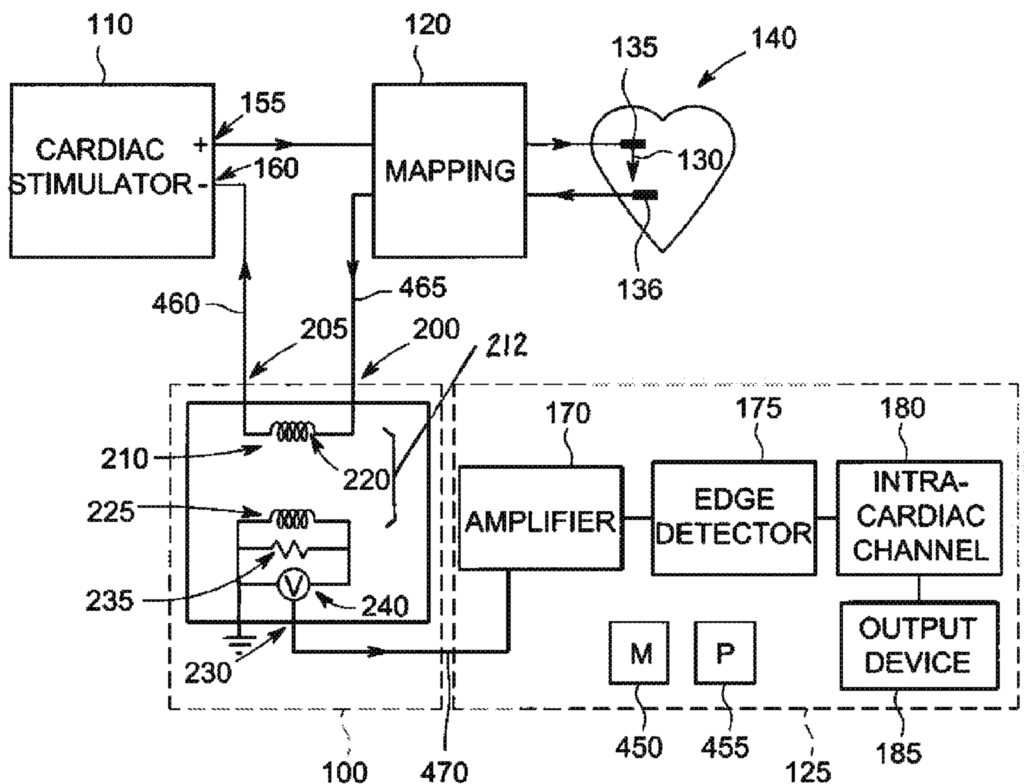
FIG. 2 shows a schematic diagram of one embodiment of a system to indirectly couple a cardiac stimulator system and an EP mapping system with an EP recording system in a procedure to apply a stimulator signal via a catheter to various locations of a subject's heart in accordance to the subject matter described herein.

FIG. 2 illustrates one embodiment of a system 100 that indirectly couples a cardiac stimulator system 110 and a mapping system 120 with an EP recording system 125 in a procedure to apply a stimulator or pacer signal 130 (e.g., electrical current) via catheters 135, 136 to various locations of a subject's heart 140 in accordance to the subject matter described herein. The system 100 in combination with the cardiac stimulator system 110, EP recorder system 125, and mapping system 120 addresses a need to detect, and record a location and time of delivery of the stimulator signal 130 used for stimulating or pacing the subject's heart 140 in a study (e.g., electrophysiology) when delivery of the signal 130 may be controlled independent of the EP recorder system 125. The system 100 also enables the generation of a display or graphic illustration of an electrical map 145 that shows a location of delivery of the stimulator signal 130 via the catheters 135, 136 to the subject's heart 140 concurrent with a display of an electrocardiogram (ECG) 150 (e.g., surface and/or intracardiac) of the subject's heart 140 during this. Although the stimulator signal 130 is shown being delivered across catheters 135, 136, other forms of delivery of the stimulator signal 130 to the subject can be employed and is not limiting on the subject matter described herein.

The cardiac stimulator system 110 generally includes a generator that can be operable to generate the stimulator signal 130 in the form of an electrical current for communication via the catheters 135, 136 to the subject's heart 140. The cardiac stimulator system 110 generally includes a positive terminal 155 and a negative terminal 160 to communicate the stimulator signal 130 through a closed electrical circuit. Examples of the cardiac stimulator system 110 include EPS320 Cardiac Stimulator by Micropace EP Inc., Bloom DTU-215B by Fischer Medical Technologies, Z6 Cardiac Simulator by ST CardioTechnologies, etc. The types of generators can vary, and can typically be either bi-phasic, or mono-phasic.

The mapping system 120 can be electrically connected to route the stimulator signal 130 from the cardiac stimulator system 110 to the catheter 135 tracked by the mapping system 120 in applying the stimulator signal 130 to various locations of the subject's heart 140 as elected by the physician. Examples of the mapping system 120 and catheters 135, 136 can include CARTO 3 by Biosense Webster, EnSite NavX by St Jude Medical, etc. The mapping system 120 can be operable to communicate the stimulator signal 130 via the catheters 135, 136 to locations of the subject's heart 140 and track locations of delivery of the stimulator signal 130 and related electrical activity of the subject's heart 140 associated therewith for illustration on the display 145 by the mapping system 120. In addition to delivering the electrical stimulator signal to the subject's heart, the mapping system 120 can be connected to close the electrical circuit in such a manner to communicate the return electrical stimulator signal 130 passing through the subject's heart 140 for communication via the system 100 to the negative terminal 160 of the cardiac stimulator system 110.

Figure 3:
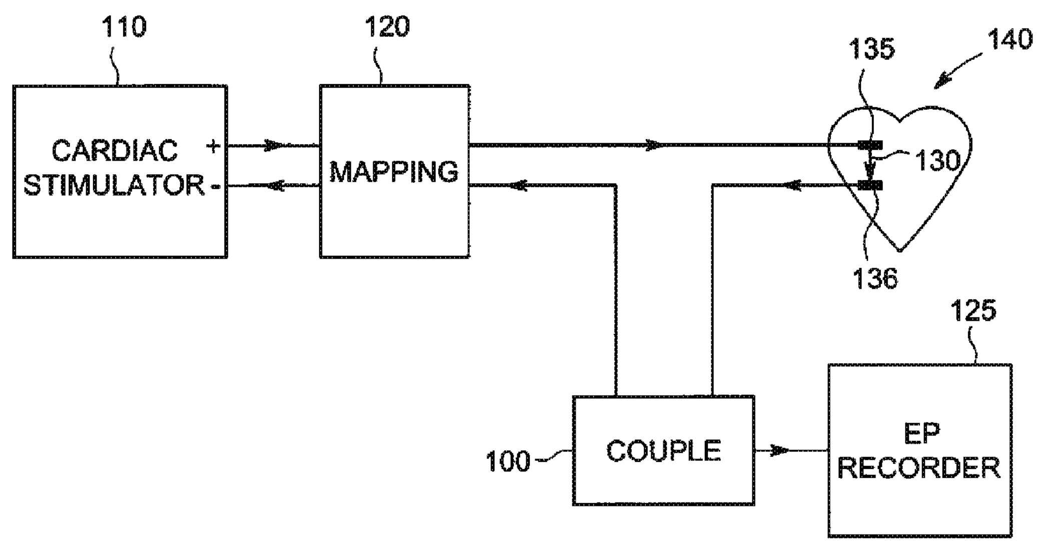
FIG. 3 shows a schematic diagram of another embodiment of the system of FIG. 2 indirectly coupling the cardiac stimulator system, the mapping system, and the EP recorder system in accordance to the subject matter described herein.
Figure 4:
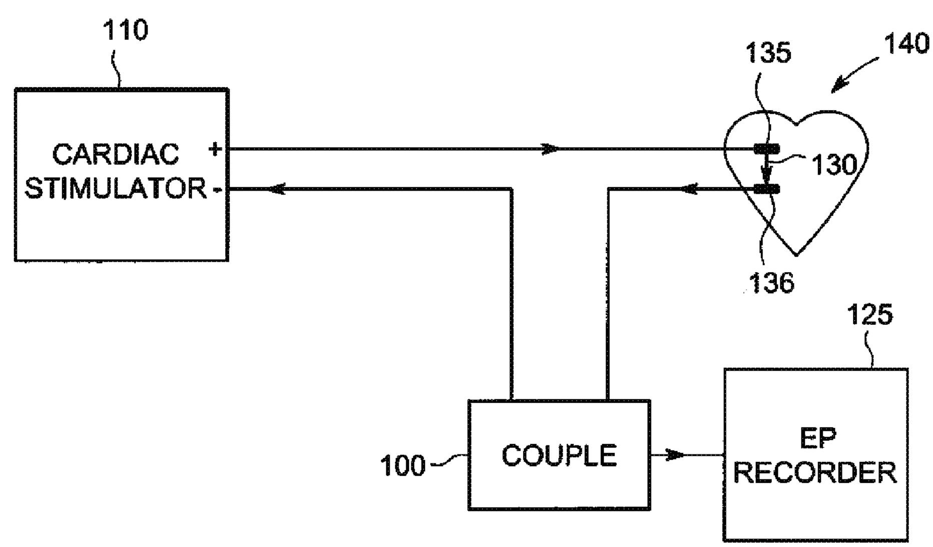
FIG. 4 shows a schematic diagram of another embodiment of the system of FIG. 2 indirectly coupling the cardiac stimulator system and the EP recorder system in accordance to the subject matter described herein.

FIG. 3 shows another embodiment of the system 100 configured to indirectly couple the EP recorder 125 in combination with the cardiac stimulator 110 and the mapping system 120. As shown, the system 100 (and EP recorder 125) can be arranged and connected between the mapping system 120 and the catheters 135, 136 in delivering the stimulator signal 130 to the subject's heart 140, in contrast to the system 100 connected between the cardiac stimulator system 110 and the mapping system 120 as shown in FIG. 2. FIG. 4 shows yet another embodiment of the system 100 configured to indirectly couple the EP recorder 125 in combination with the cardiac stimulator 110, without combination with the mapping system 120. As shown, the system 100 (and EP recorder 125) can be connected between the cardiac stimulator system 110 and the catheters 135, 136 in delivering the stimulator signal 130 to the subject's heart 140. Thus, FIGS. 2 through 4 illustrate that the system 100 can be configured to interconnect with the cardiac stimulator system 110 with the EP recorder system 125 (and the mapping system 120 if needed) in a desired manner as described herein such that the electrical load or impedance of the EP recorder system 125 is not placed on the cardiac stimulator system 110.

The EP recorder system 125 can be operable to acquire surface or intracardiac ECG signals of the subject's heart 140 concurrent with application of the stimulator signal 130 via the catheters 135, 136 to the subject's heart 140 and mapping of the subject's heart 140. One embodiment of the EP recorder system 125 can generally include an amplifier 170 connected in communication with an edge detector system 175, an intracardiac channel 180, and an output output device 185. Examples of the EP recorder system 125 can include CardioLab by General Electric Company, EP WorkMate by St Jude Medical, Lab System Pro by Bard, etc.

Referring back to FIG. 2, one embodiment of the system 100 of the subject matter described herein generally indirectly connects the EP recorder system 125 in electrical communication with the cardiac stimulator system 110 and the mapping system 120. The system 100 can include a first terminal 200 connected to receive a return electrical stimulator signal 130 passing from the subject's heart 140 and through the mapping system 120. The system 100 can include a second terminal 205 connected to communicate the return stimulator signal 130 received at the first terminal 200 of the system 100 to the negative terminal 160 of the cardiac stimulator system 110.

Electrically connected between the first and second terminals 200, 205 of the system 100 can be an indirect electrical couple 210. One embodiment of the indirect electrical couple 210 can be a transformer 212 having a first winding 220 and second winding 225. The first winding 220 can be in hard or direct electrical connection between the first and second terminals 200, 205. The second winding 225 can be connected in hard or direct electrical connection with a third terminal or output terminal 230 of the system 100. The windings 220, 225 can be configured (e.g., a coil) in a known manner such that a first signal (e.g., stimulator signal 130) through the first winding 220 can induce a second or secondary signal to be generated from the second winding 225.

The system 100 can further include a resistor 235 and meter 240 electrically connected in parallel with the second winding 225. The resistor 235 in combination with the meter 240 can be connected to communicate an output signal from the meter 240 of the voltage reading of the secondary signal across the resistor 235 for output from the third terminal 230 to the EP recorder system 125. The third terminal 230 can connected to communicate the output signal from the system 100 to the amplifier 170 of the EP recorder system 125 for signal processing and illustration on the output device 185 in combination with the ECG signal 150 acquired by the EP recorder system 125, or independent thereof, concurrent with the procedure to apply the stimulator signal 130 to the subject's heart 140.

Figure 5:
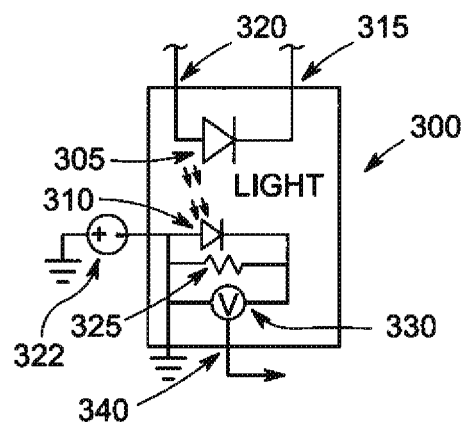
FIG. 5 illustrates a detailed schematic diagram of another embodiment of a system that indirectly couples a cardiac stimulator system and an EP mapping system with an EP recording system in a procedure to apply a stimulator signal via a catheter to various locations of a subject's heart in accordance to the subject matter described herein.

FIG. 5 shows an embodiment of a system 300 configured and operable in a similar manner to the system 100 as shown in FIG. 2 to indirectly couple the EP recorder system 125 in combination with the cardiac stimulator system 110 and mapping system 120. The system 300 can include another embodiment of the indirect couple 210 (see FIG. 2) having a light emitting device (e.g., LED or light emitting diode, light emitting transducer, etc.) 305 in combination with a light receiving or detecting device (e.g., photodiode, light receiving transducer, etc.) 310. The light emitting device 305 can be directly connected between the first and second electrical terminals 315, 320 similar to terminals 200, 205 in FIG. 2, such that the first signal (e.g., the stimulator signal 130) across the light emitting device 305 causes an transmission of light across to the light receiving or detecting device 310. The light detecting device 310 can be configured to generate the second signal in response to receiving or detecting the light transmitted from the light emitting device 305. The light detecting device 310 can be electrically connected with an electrical power supply or source 322, a resistor 325, and/or a voltmeter 330 so as to communicate an output signal, representative of the voltage reading of the secondary signal detected by the voltmeter 330 across the resistor 325, for output from the third terminal 340 to display at the output device 185 of the EP recorder system 125 or independent thereof, similar in manner to the embodiment of the terminal 230 shown in FIG. 2.

Figure 6:
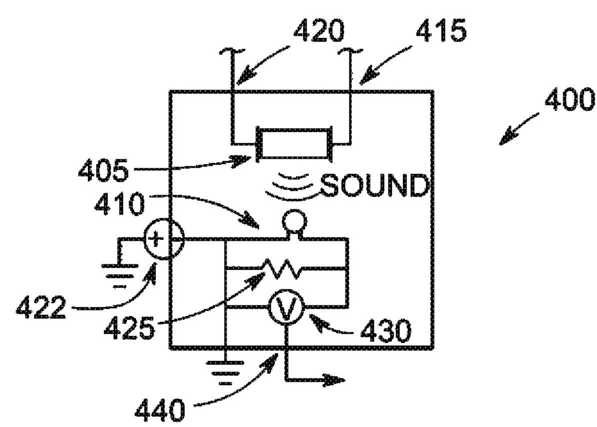
FIG. 6 illustrates a detailed schematic diagram of yet another embodiment of a system that indirectly couples an electrical stimulator system and an electrical mapping system with an EP recording system in a procedure to apply a stimulator signal via a catheter to various locations of a subject's heart in accordance to the subject matter described herein.

FIG. 6 shows yet another embodiment of a system 400 configured and operable in a similar manner to the system 100 as shown in FIG. 2 that indirectly couples the EP recorder system 125 in combination with the cardiac stimulator system 110 and mapping system 120. The system 400 can include another embodiment of the indirect couple 210 (see FIG. 2) having a sound generator device (e.g., radio frequency signal generator, ultrasound signal generator, a sound transmitting transducer, etc.) 405 in combination with a sound receiving or detecting device (e.g., microphone, sound receiving transducer, etc.) 410. The sound generating device 305 can be directly connected between the first and second electrical terminals 415, 420 similar to terminals 200, 205 in FIG. 2, such that the first signal (e.g., the stimulator signal 130) across the sound generating device 405 causes an transmission of sound across to the sound receiving or detecting device 410. The sound detecting device 410 can be configured to generate the second signal in response to receiving or detecting the sound transmitted from the sound generating device 405. The sound detecting device 410 can be electrically connected with an electrical power supply or source 422, a resistor 425 and/or voltmeter 430 so as to communicate an output signal, representative of the voltage reading by the voltmeter 430 of the secondary signal across the resistor 425, for output from a third terminal 440 to display at the output device 185 of the EP recorder system 125 or independent thereof, similar in manner to the embodiment of the system 100 shown in FIG. 2.

Although the embodiments of the systems 300 and 400 are described with reference to indirectly electrical coupling the EP recorder system 125 with the cardiac stimulator system 110 and mapping system 120 as shown in FIG. 2, it should be understood that the embodiments of the system 300 and 400 or one or more components thereof can be arranged and interconnected in a manner similar to the system 100 shown in FIGS. 5 and 6 and is not limiting on the subject matter described herein.

The above described construction of the system 100, 300, and 400 in combination with the cardiac stimulator system 110, EP recorder system 125 and/or the mapping system 120 in more than one way and should not be limiting on the subject matter described herein.

In one example, herein referred to as the "Accessory Mode", the system 100 can be packaged within a T-type configuration having one cable connector 460 from the terminal 200 to the cardiac stimulator system 110, second cable connector 465 from the terminal 200 that connects to the mapping system 120, and the third cable connector 470 that connects the terminal 230 to the EP recorder system 125. The system 100 can further include a branch cable that connects the output signal generated via the second winding 225 of the transformer 212 in the T-type cable for communication to the amplifier 170 of the input of the EP recorder system 125. This branch cable can represent the secondary winding 225 of the transformer 212.

In another example, herein referred to as "Embedded Mode", the cardiac stimulator system 110 can be connected to a "Passive Stim" input on an amplifier (not shown) of the mapping system 120. The return stimulator signal 130 can be routed through the primary winding 210 of the transformer 212, and to a second connector "Active Stim Out". This second connector links the primary winding 220 of the transformer 212 to the EP mapping system 120 where it is routed to the respective catheter 135. The secondary winding 225 of the transformer located within the amplifier 170 of EP recorder system 125 can be connected to a dedicated passive stimulator amplifier input of the mapping system 120.

Having generally provided the above-description of a construction of the embodiments the system 100 of the subject matter described herein, the following is a general description of a method of operation of the system 100 in combination with the cardiac stimulator system 110, the mapping system 120, and the EP recording system 125. It should also be understood that the sequence or succession of the acts or steps of the method as described in the foregoing description can vary. Also, it should be understood that the method may not require each act or step in the foregoing description, or may include additional acts or steps not disclosed herein. One or more of following steps and acts of the method can also be in the form of computer-readable program instructions stored on a computer readable medium or memory (e.g., hard drive of a computer, CD, DVD, flash drive, etc.) 450 for execution by a processor 455 of a computer programmable device at the EP recorder system 125 or independent thereof.

The cardiac stimulator system 110 can operate as a constant current source in generating a stimulator signal for delivery or application to the cardiac tissue of the subject's heart 140. The stimulator system 110 can compensate for inherent losses in the wiring and components to deliver the indicated amplitude of electrical current or energy via the stimulator signal 130 to the cardiac tissue of the subject's heart 140.

The system 100 can generally isolate the electrical load or impedance of the EP recorder system 125 from the cardiac stimulator signal source—in this case the electrical stimulator system 110. Among other technical effects, the system 100 can prevent electrical losses associated with electrical load on the cardiac stimulator system 110 from exceeding the available energy that can be delivered from the cardiac stimulator system 110, which otherwise could cause a consequential reduction in a delivery of stimulation signal 130 to the subject's heart 140. Additionally, the system 100 can prevent the cardiac stimulator system 110 from sensing an unexpected additional electrical load that could otherwise cause a fault condition that prevents delivery (e.g. register a high impedance fault) of any stimulator or pacing signals 130 to the subject's heart.

The primary winding 220 of the transformer 212 conducts the stimulator signal 130 with minimal additional impedance load while being in direct connection to the EP mapping system 120. The system 100 in combination with the EP recorder system 125 and EP mapping system 120 can allow the routing of the stimulator signal 130 to the catheters 135, 136 with minimal electrical loading on the cardiac stimulator system 110. Receiving or detecting communication of the return stimulator signal 130 at the first terminal 200 and across the primary winding 220 of the transformer 212 causes the secondary winding 220 to generate a voltage differential across the resistor 235 for detection by the meter 240. In response, the meter 240 generates the output signal for communication to the amplifier 170 of the EP recorder 125. The secondary winding 225 of the transformer 212 can be electrically connected to the high input impedance amplifier 170 and treated as the "virtual" stimulator or pacing signal for the purposes of illustration of occurrence at the output device 185 of the EP recorder system 125. This output signal can be included for display and recording in combination with acquired ECG signal or waveform 150 acquired from the subject during delivery of the stimulator signal 130 to the subject's heart 140. This method of operation of the system 100 allows a user to immediately view the acquired ECG waveform 150 and relationship to the delivery of the stimulator signal 130 in a similar manner as if the EP recorder system 125 were not in the path of the simulator signal 130. The communication of the stimulator signal 130 through the primary winding 220 induces an electrical current or secondary signal through the secondary winding 225 of the transformer 212. This secondary signal (e.g., electrical current) causes a voltage differential across the resistor 235. The meter 240 can be connected to detect this voltage differential and communicate the secondary signal via the output 200 to the amplifier 170 of the EP recorder system 125. The EP recorder system 125 can amplify, digitize, and modify the secondary signal to have desired electrical pulse parameters (e.g., amplitude, width, etc.) in response to user inputs for illustration on the output device 185.

Figure 7:
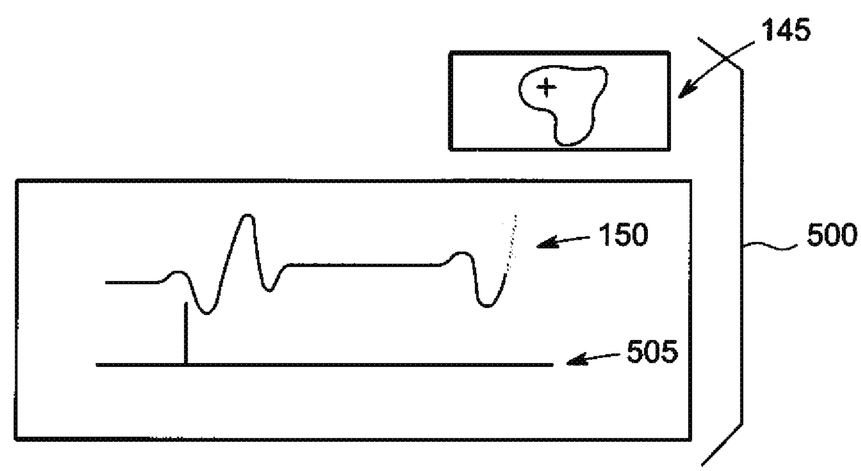
FIG. 7 illustrates a schematic diagram of an embodiment of a display generated by the system of FIG. 2, 3 or 4 in accordance with the subject matter described herein.

Referring to FIGS. 2 and 7, an example schematic diagram of an embodiment of a display 500 generated at the output device 185 of the EP recorder system 125 is provided for illustration at the output device 185 or independent thereof. The display 500 can include a first graphic illustration of the ECG signal 150 acquired by the EP recorder system 125 (See FIG. 2) during the procedure to apply the electrical stimulator signal 130 to the subject's heart 140 concurrent with the display or graphic illustration 145 of the mapping of the electrical activity of the subject's heart 140 by the mapping system 120. The display 500 can illustrate the first graphic illustration 150 in combination or concurrent with a second graphic illustration 505 of detection of delivery of the stimulator signal 130 to various locations (as tracked by the mapping system 120) of the subject's heart 140.

Technical effects of the above-described embodiments of the system 100 and method can include: isolating the cardiac stimulator system 110 from the input to the amplifier 170 associated with the EP recorder system 125; isolating the inherent impedance load associated with the EP recorder system 125 from the EP mapping system 120 and the cardiac stimulator system 110 (associated with the design of the indirect detection of the stimulator signal 130, the system 100 does not introduce an additional energy source into the electrical circuit of the cardiac stimulator system 110); reduction in the impedance loading on the cardiac stimulator system 110 so as to maximize delivery of energy to the subject's heart 140; and avoidance of a need to introduce a switching network that would increase opportunities to introduce potential sources of noise to the circuit and the EP recording system 125 and mapping system 120.

Additional technical effects of the system 100 include providing an ability to retrofit this into a customer environment with the above-described constructions of the system 100 provided herein; providing a dedicated electrical connection to the cardiac stimulator system 110; reducing opportunities to introduce sources of noise attenuation to the mapping system 120 and EP recorder system 125; an ability to be retrofit with various types of mapping systems 120 with minimal changes; and to provide application and retrofit in the field.

The subject matter described herein provides a system 100 that can detect an occurrence of the stimulator or pacer signal 130 delivered by a stimulator system 110 via an EP mapping system 120 to a subject's heart 140 for illustration on the output device 185 in combination with real-time acquisition of the ECG waveform 150 of the subject without loading an impedance of an EP recorder system 125 on the delivery of the stimulator signal 130 to the subject's heart 140. The subject matter described herein also provides a system 100 in combination with a stimulator system 110, the EP recorder system 125, and the EP mapping system 120 in delivering the stimulator signal 130 to the subject's heart 140. The EP recorder system 125 can be operable to acquire ECG from the subject, the system 100 comprising an electrical coupling 210 that communicates the stimulator signal 130 between the EP mapping system 120 and the stimulator system 110 without loading an impedance of the EP recorder system 125 on delivery of the stimulator signal 130 to the subject's heart 140. The EP recorder system 125 can generate the display 500 that includes graphic illustration 505 of the detection of the time or occurrence of delivery of the stimulator signal 130 to the subject's heart 140 in combination with and relative to acquired ECG waveform 150 of the subject during delivery of the stimulator signal 130 to the subject's heart 140.

A method of delivering the stimulator signal 130 to subject's heart 140 is provided in the subject matter described herein. The method includes the steps of communicating or routing the stimulator signal 130 through the EP mapping system 120 for delivery by the catheter 135 of the EP mapping system 120 to the heart of a subject; creating the map that shows locations of the delivery of the stimulator signal 130 to the subject's heart 140; and creating the display 145 at the EP recorder 125 that includes the illustration 505 of an occurrence of or time of delivery of the stimulator signal 130 to the subject's heart 140 in combination with and relative to the illustration 150 of the ECG waveform acquired from the subject while delivering the stimulator signal 130. The EP recorder 125 is not in electrical connection to receive the stimulator signal 130 or portion thereof.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A system in combination with a stimulator system and an electrophysiology recorder system in delivering a stimulator signal to a subject's heart, the electrophysiology recorder system operable to acquire an electrocardiogram from the subject's heart, the system comprising:

an electrical coupling in electrical connection between the simulator system and the electrophysiology recorder, where the electrical coupling communicates the stimulator signal between the stimulator system without loading an impedance of the electrophysiology recorder system on the stimulator system and generates a second electrical signal in indirect response to the electrical coupling communicating the stimulator signal returning from the subject's heart to the stimulator system; and a meter that generates an output signal in response to detection of the second electrical signal generated by the electrical coupling, wherein the meter communicates the output signal to the electrophysiology recorder system for illustration on a display in combination with the electrocardiogram of the subject's heart acquired in real-time by the electrophysiology recorder system.

2. The system of claim 1, wherein the electrophysiology recorder system generates a display of a detection of delivery of the stimulator signal to the subject's heart in combination with the electrocardiogram of the subject during delivery of the stimulator signal to the subject's heart.

3. The system of claim 1, wherein the electrophysiology recorder system does not control delivery of the stimulator signal to the subject's heart.

4. The system of claim 1, wherein the electrical coupling includes a first terminal to receive a return of the electrical stimulator signal from the subject's heart, and a second terminal to communicate return of the stimulator signal received at the first terminal back to the stimulator system.

5. The system of claim 4, wherein the electrical coupling includes a transformer having a primary winding in inductive relation to a secondary winding, the primary winding in electrical connection between the first and second terminals, and the secondary winding in electrical connection to the meter.

6. The system of claim 4, wherein the electrical coupling includes a light emitting device in spatial relation to a light detecting device, the light emitting device electrically connected between the first and second terminals such that receiving the stimulator signal causes the light emitting device to generate a light signal that causes generation of the second signal by the light detecting device.

7. The system of claim 4, wherein the electrical coupling includes a sound generating device in spatial relation to a sound detecting device, the sound generating device electrically connected between the first and second terminals such that receiving the stimulator signal causes the sound generating device to generate a signal that causes generation of the second signal at the sound detecting device.

8. The system of claim 4, the system further including a resistor in electrical connection with the meter, wherein the second electrical signal creates a voltage differential across the resistor for detection by the meter.

9. The system of claim 4, wherein the electrophysiology recorder system is not in direct connection to receive the stimulator signal generated by the stimulator system.

* * * * *